US006847586B1

(12) United States Patent
Chen

(10) Patent No.: US 6,847,586 B1
(45) Date of Patent: Jan. 25, 2005

(54) PORTABLE HUMAN HEIGHT MEASURING DEVICE

(76) Inventor: Paul Ping Zhi Chen, 1188 Kottinger Dr., Pleasanton, CA (US) 94566

( * ) Notice: Subject to any disclaimer, the term of this patent is extended or adjusted under 35 U.S.C. 154(b) by 0 days.

(21) Appl. No.: 10/617,581

(22) Filed: Jul. 11, 2003

(51) Int. Cl.$^7$ ............................................... G01S 15/00
(52) U.S. Cl. ......................... 367/99; 367/108; 367/115; 367/116
(58) Field of Search ........................... 367/99, 108, 115, 367/116

(56) References Cited

U.S. PATENT DOCUMENTS

| | | |
|---|---|---|
| 442,192 A | 12/1890 | Lewis |
| 1,377,671 A | 5/1921 | Dieckmann |
| 2,215,884 A | 9/1940 | Runge |
| 2,736,100 A | 2/1956 | Landau |
| 3,313,030 A | 4/1967 | Heys |
| 4,134,212 A | 1/1979 | Allen |
| 4,134,213 A | 1/1979 | Kushmuk |
| 4,196,521 A | 4/1980 | Hutchinson |
| 4,412,384 A | 11/1983 | Viets |
| 4,694,581 A | 9/1987 | Heinrich |
| 5,379,028 A | 1/1995 | Chung |
| 5,402,585 A | 4/1995 | Lund |
| 5,813,132 A | 9/1998 | Bodkin |
| 6,003,235 A | 12/1999 | Chen |
| 6,011,754 A * | 1/2000 | Burgess et al. ............. 367/116 |
| 6,073,359 A | 6/2000 | Lee |
| 6,226,881 B1 | 5/2001 | Landauer |
| 6,237,239 B1 | 5/2001 | Miyazaki |
| 6,327,494 B1 | 12/2001 | Sakai |

FOREIGN PATENT DOCUMENTS

| | | | | |
|---|---|---|---|---|
| JP | 1055132 | * | 2/1998 | ............ G09B/9/00 |

* cited by examiner

Primary Examiner—Daniel Pihulic

(57) ABSTRACT

The invention is a portable human height measuring device. The device consists of an ultrasonic distance sensor, a controller and several output units. The ultrasonic distance sensor measures a person's height. The control unit converts the electronic signals from the ultrasonic sensor to proper measuring standards. The measurement output units displays, announces, or/and prints the measurement. The device is integrated onto a baseball like cap. The ultrasonic sensor is mounted on the sun visor of the cap. The control and output units are mounted on the crown of the cap. A switch is mounted on the top of the inner cap. When the head of the person wearing the cap touches the switch, it triggers the ultrasonic sensor to start measuring. The person's height is then converted to the proper measuring unit, and communicated to the person via output units.

4 Claims, 4 Drawing Sheets

Perspective View

Fig.1 Perspective View
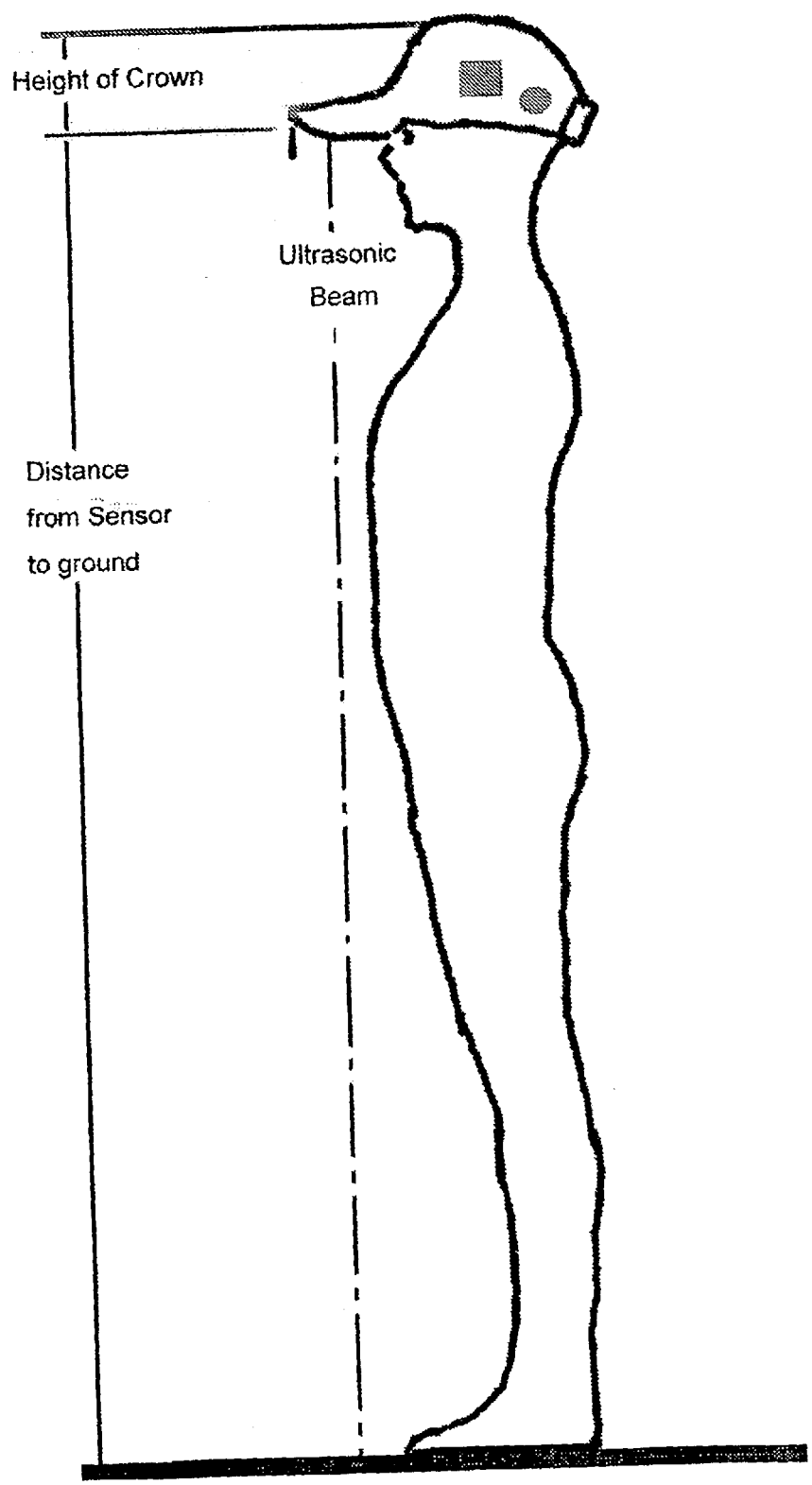

Fig. 2 Over View
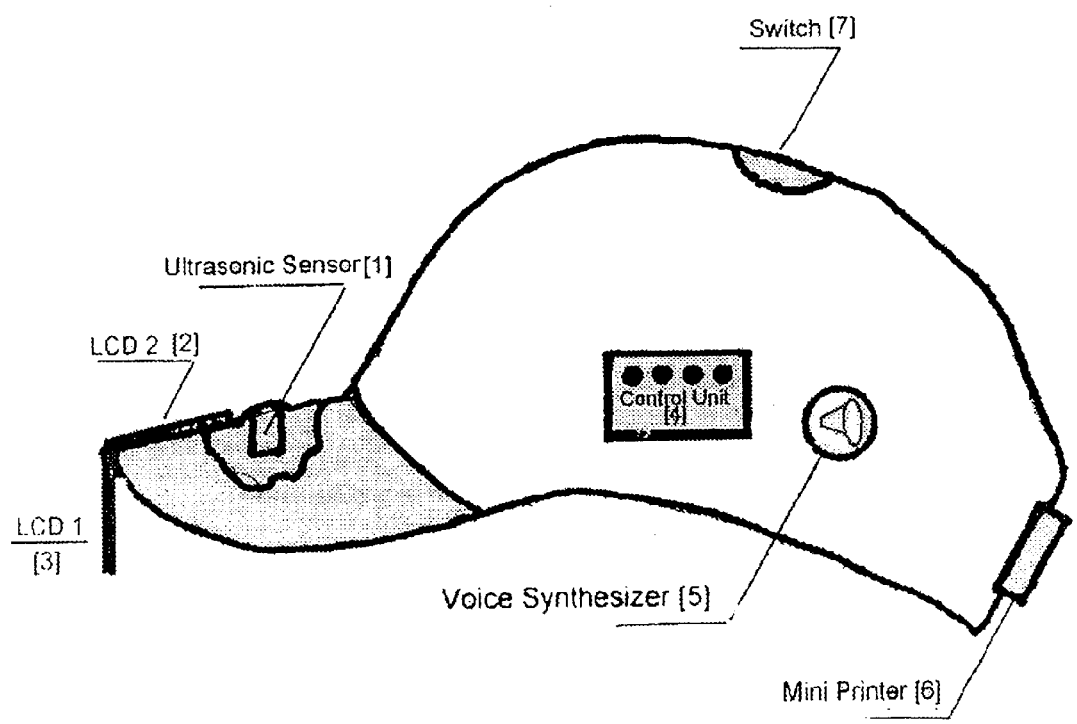

Fig.3 Front View
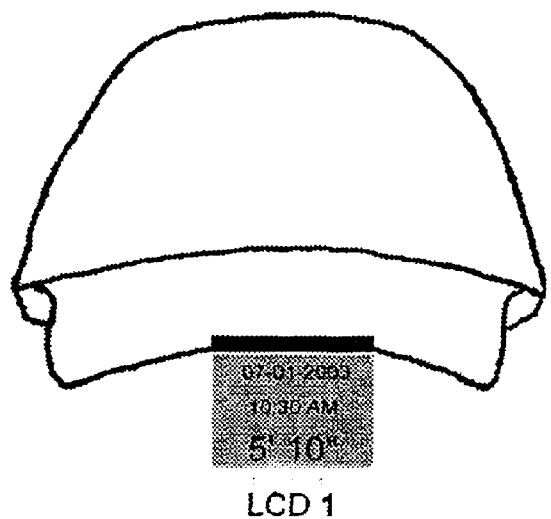
LCD 1
Fig.4 Top View
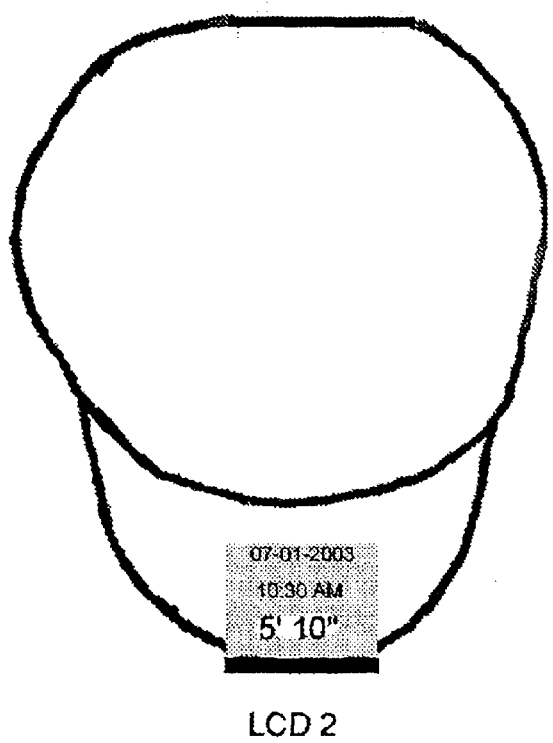
LCD 2

Fig.5 Back View
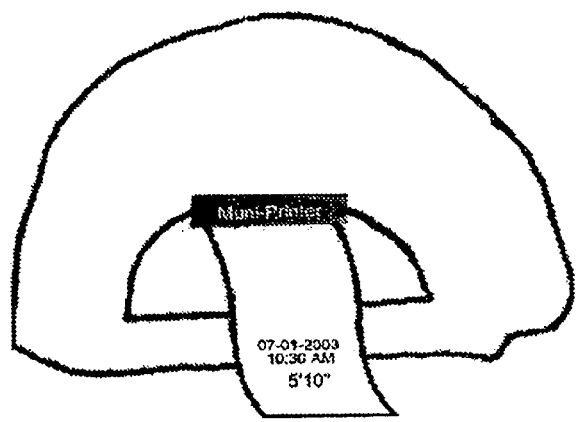
Fig.6 Voice Synthesizer
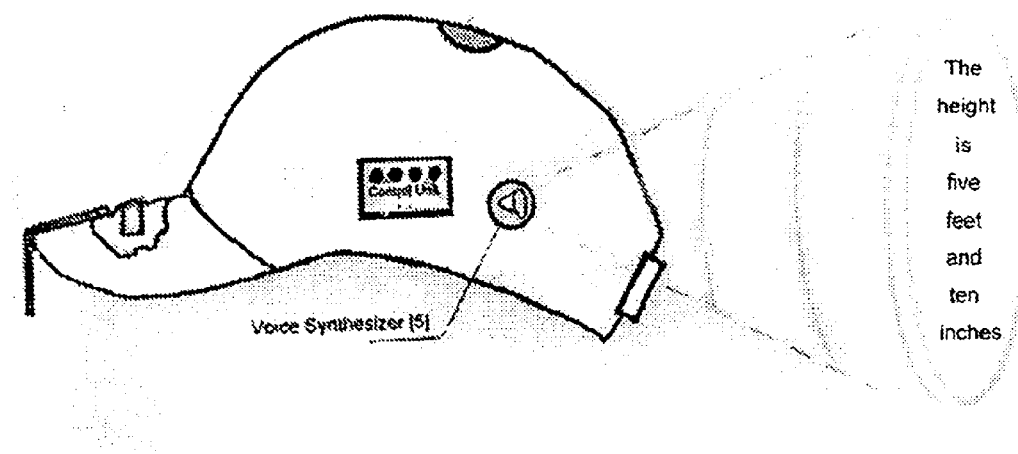

PORTABLE HUMAN HEIGHT MEASURING DEVICE

BACKGROUND OF THE INVENTION

Height is one of the important characteristics for a person. People, especially growing children are eager to know their height and their growth rate. In addition, the change in height for an elderly or a patient is also important diagnosis information for his or her doctor.

From Dec. 9, 1890 U.S. Pat. No. 442,192 to the recent Dec. 4, 2001 U.S. Pat. No. 6,327,494, all the devices invented use graduated scale with movable rectangular frame for measurement. These devices are bulky, heavy, and difficult to transport. For portability, May 8, 2001 U.S. Pat. No. 6,226,881, Jun. 13, 2000 U.S. Pat. No. 6,073,359 etc. make the scale stand and frame collapsible, foldable or able to elongate.

Nov. 1, 1983 U.S. Pat. No. 4,412,384 uses an extensible tape instead of solid scale stand. On the frame there is a level indicator indicating its level state in order to measure the highest point of the person.

Jan. 3, 1995 U.S. Pat. No. 5,379,028 uses audio signal to report the height measured on a mechanical slide.

All these devices have a graduated measure upright stand or a plate hanged on the wall, a level ruler and a flat ground plate. They are bulky and difficult to move.

Therefore, the inventor creates a portable human height measuring device integrated onto a cap which is easy to carry and use. It can measure the height of the person on, any flat ground.

This portable human height measuring device invention is thoroughly different from the prior and related arts. My invention uses an ultrasonic distance sensor and control unit integrated onto a cap to measure the height. The accuracy and precision of measurement can match any graduated scale. This invention has seven (7) measuring output choices:
1. Visual—LCD display;
2. Audio—voice synthesizer;
3. Printout—printer output;
4. Visual and audio;
5. Visual and printout;
6. Audio and printout;
7. Visual, audio and printout.

The printer output records the height measurement and the date of measurement. This data could be collected over time to calculate a person's growth rate.

With all these functions, the portable human height measuring device is still light and compact. It is easy to use, control and carry.

DESCRIPTION

FIG. 1 is a perspective view of a person wearing a cap with integrated portable human height measuring device standing on the flat ground. The height of the person being measured is the distance from the cap visor to the ground measured by the ultrasonic sensor, plus the height of the cap crown.

FIG. 2 shows the overview of the portable human height measuring device. The device has an ultrasonic sensor placed on the sun visor of the cap [1], a liquid crystal display mounted on the tip of the sun visor [2] and [3], a control unit [4], a voice synthesizer [5], a mini printer [6] mounted on the crown of the cap, and a switch on inner top of the cap [7].

FIG. 3 is a sketch of the front view of the portable human height measuring cap. The LCD mounted on the sun visor is flipped down and shows the height measurement in English standard.

FIG. 4 is a sketch of the top view of the portable human height measuring cap with the LCD flipped up.

FIG. 5 shows the back of the cap equipped with a mini-printer. The printer outputs the height measurement and the date the height measurement is taken.

FIG. 6 shows a portable human height measuring cap equipped with a voice synthesizer. The speaker announces the height measurement in English.

OPERATION

1. Have the person being measured standing upright on a flat ground. FIG. 1
2. Put the cap on the head of the person. The device switches on when the person's head touches the switch.
3. After the device is turned on, the ultrasonic distance sensor sends the distance between the cap visor and the ground to the control unit.
4. Upon receiving the distance measurement from the ultrasonic sensor, the control unit calculates the-person's height by adding the height of the cap crown to the measurement from the ultrasonic sensor.
5. The control unit converts the measurement to the proper unit, inches for English system or meters for metric system; and sends the result to the output unit(s).
6. The output units then present the height measurement with LCD display, or/and readout or/and printout.

There are several selections on the control unit:
1. A combination of LCD, audio device, mini-printer to report the height. There are seven (7) selections.
2. The standard of height in metric or English system.
3. The language selection for the audio output.
4. Set the date and time.
5. Device calibration.

Although the present invention has been described in considerable detail with reference to certain preferred versions thereof, other versions are possible. Therefore, the spirit and scope of the appended claims should not be limited to the description of the preferred versions contained herein.

I claim:

1. A portable human height measuring device, that comprising an ultrasonic distance sensor and a control unit integrated onto a cap, with means to measure human height either in metric or English system.

2. The portable human height measuring device according to claim 1 wherein said the height measurement can be shown on a LCD mounted on the sun visor of the cap.

3. The portable human height measuring device according to claim 1 wherein said the height measurement can be announced via a voice synthesizer mounted on the crown of the cap based on a selected language, this capability enables a visually impaired person to measure his or her own height.

4. The portable human height measuring device according to claim 1 wherein said the height measurement and the date of the measurement can be printed out via a mini printer mounted on the crown of the cap, this data could be collected over time to calculate a person's growth rate.

* * * * *